United States Patent
Fu et al.

(10) Patent No.: US 10,324,046 B1
(45) Date of Patent: Jun. 18, 2019

(54) METHODS AND SYSTEMS FOR MONITORING A NON-DEFECT RELATED CHARACTERISTIC OF A PATTERNED WAFER

(71) Applicant: KLA-Tencor Corporation, San Jose, CA (US)

(72) Inventors: Tao-Yi Fu, Fremont, CA (US); Steve Lange, Alamo, CA (US); Lisheng Gao, Morgan Hill, CA (US); Xuguang Jiang, Santa Clara, CA (US); Ping Gu, Milpitas, CA (US); Sylvain Muckenhirn, Santa Barbara, CA (US)

(73) Assignee: KLA-Tencor Corp., San Jose, CA (US)

( * ) Notice: Subject to any disclaimer, the term of this patent is extended or adjusted under 35 U.S.C. 154(b) by 226 days.

(21) Appl. No.: 15/241,005

(22) Filed: Aug. 18, 2016

Related U.S. Application Data

(63) Continuation of application No. 12/477,508, filed on Jun. 3, 2009, now abandoned.

(51) Int. Cl.
| | |
|---|---|
| *G01N 21/00* | (2006.01) |
| *G01N 21/95* | (2006.01) |
| *G01B 11/30* | (2006.01) |
| *G01N 21/956* | (2006.01) |
| *G01N 21/88* | (2006.01) |
| *H01L 21/66* | (2006.01) |

(52) U.S. Cl.
CPC ....... *G01N 21/9501* (2013.01); *G01B 11/303* (2013.01); *G01N 21/8806* (2013.01); *G01N 21/956* (2013.01); *H01L 22/12* (2013.01)

(58) Field of Classification Search
USPC .......................................................... 702/4
See application file for complete search history.

(56) References Cited

U.S. PATENT DOCUMENTS

| | | | | |
|---|---|---|---|---|
| 5,640,237 | A * | 6/1997 | Esrig ................. | G01N 21/8806 356/237.2 |
| 5,996,415 | A * | 12/1999 | Stanke ................. | G01N 29/041 374/119 |
| 2007/0229809 | A1* | 10/2007 | Belyaev ............. | G01N 21/9501 356/237.2 |
| 2008/0013083 | A1* | 1/2008 | Kirk ................... | G01N 21/4738 356/237.5 |
| 2008/0018887 | A1* | 1/2008 | Chen ...................... | G01N 21/47 356/237.2 |
| 2009/0299655 | A1* | 12/2009 | Biellak ................... | H01L 22/12 702/40 |
| 2010/0060888 | A1* | 3/2010 | Reich ................. | G01N 21/9501 356/237.5 |
| 2010/0188657 | A1* | 7/2010 | Chen .................. | G01N 21/9501 356/237.5 |

\* cited by examiner

*Primary Examiner* — Paul D Lee
(74) *Attorney, Agent, or Firm* — Ann Marie Mewherter

(57) ABSTRACT

Methods and systems for monitoring a non-defect related characteristic of a patterned wafer are provided. One computer-implemented method includes generating output responsive to light from a patterned wafer using an inspection system. The method also includes determining differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic.

20 Claims, 1 Drawing Sheet

METHODS AND SYSTEMS FOR MONITORING A NON-DEFECT RELATED CHARACTERISTIC OF A PATTERNED WAFER

BACKGROUND OF THE INVENTION

1. Field of the Invention

The present invention generally relates to methods and systems for monitoring a non-defect related characteristic of a patterned wafer. Certain embodiments relate to monitoring a non-defect related characteristic of a patterned wafer using an inspection system.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined using currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on the wafer such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Furthermore, using metrology tools to measure characteristics across the wafer for inline monitoring and control applications is not feasible due to the time in which such measurements can be performed. In particular, metrology measurements performed by currently available metrology tools such as surface roughness, resistivity, film thickness, etc. are not suitable for high sampling of wafers for inline monitoring since the measurements will impact (e.g., increase) cycle time in production.

Accordingly, it would be advantageous to develop methods and systems that can be used for monitoring a non-defect related characteristic of a patterned wafer (e.g., for high sampling of wafers in applications such as inline monitoring and control of semiconductor fabrication processes without increasing the cycle time in production).

SUMMARY OF THE INVENTION

The following description of various embodiments of methods, computer-readable media, and systems is not to be construed in any way as limiting the subject matter of the appended claims.

One embodiment relates to a computer-implemented method for monitoring a non-defect related characteristic of a patterned wafer. The method includes generating output responsive to light from a patterned wafer using an inspection system. The method also includes determining differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic.

In one embodiment, the output and the other output include image data. In another embodiment, one or more parameters of the inspection system used for generating the output render the output unsuitable for use in detecting defects on the patterned wafer. In an additional embodiment, one or more parameters of the inspection system used for generating the output are different than one or more parameters of the inspection system used to generate additional output for the patterned wafer, and the additional output can be used to detect defects on the patterned wafer.

In one embodiment, generating the output is performed using only one set of parameters of the inspection system. In another embodiment, generating the output is performed such that the output is generated using more than one set of parameters of the inspection system. In an additional embodiment, the method includes selecting one or more parameters of the inspection system to be used for generating the output based on information about patterned features formed on the patterned wafer, information about the inspection system, and the non-defect related characteristic.

In one embodiment, generating the output is performed for only one or more sets of selected areas on the patterned wafer. In another embodiment, determining the differences is performed for only one or more sets of selected areas on the patterned wafer based on the differences between the one or more attributes of the output generated for only the one or more sets of selected areas on the patterned wafer and the one or more attributes of the other output for only one or more corresponding sets of selected areas on the different patterned wafer. In an additional embodiment, the method includes selecting one or more sets of areas on the patterned wafer, and determining the differences is performed for only the one or more sets of selected areas on the patterned wafer based on the differences between the one or more attributes of the output generated for only the one or more sets of selected areas on the patterned wafer and the one or more attributes of the other output for only one or more corresponding sets of selected areas on the different patterned wafer. In one such embodiment, all patterned features formed in the one or more sets of selected areas have substantially the same characteristics.

In one embodiment, determining the differences is performed based on a correlation between the differences between the one or more attributes of the output and the one or more attributes of the other output and the differences between the value and the known value. In another embodiment, determining the differences is performed based on a correlation between the differences between the one or more attributes of the output and the one or more attributes of the other output and a linear combination of the differences between the value and the known value and differences between a value of at least one other non-defect related characteristic of the patterned wafer and a known value of the at least one other non-defect related characteristic of the different patterned wafer. In an additional embodiment, determining the differences includes simultaneously determining the differences between the value and the known value and differences between a value of at least one additional non-defect related characteristic of the patterned wafer and a known value of the at least one additional non-defect related characteristic of the different patterned wafer based on the differences between the one or more attributes of the output and the one or more attributes of the other output.

In one embodiment, the one or more attributes of the output and the other output include one or more statistical attributes. In another embodiment, the method includes generating the other output of the inspection system for the different patterned wafer by using the inspection system to scan the different patterned wafer. In an additional embodiment, the method includes generating the other output of the inspection system for the different patterned wafer by simulating the other output that would be generated by the inspection system for the different patterned wafer. In a further embodiment, the output is responsive to light scattered from the patterned wafer, and generating the output does not involve Fourier filtering.

Each of the steps of each of the embodiments of the computer-implemented method described above may be further performed as described herein. In addition, each of the embodiments of the computer-implemented method described above may include any other step(s) of any other method(s) described herein. Furthermore, each of the embodiments of the computer-implemented method described above may be performed by any of the systems described herein.

Another embodiment relates to a computer-readable medium that includes program instructions executable on a computer system for performing a computer-implemented method for monitoring a non-defect related characteristic of a patterned wafer. The computer-implemented method includes generating output responsive to light from a patterned wafer using an inspection system. The method also includes determining differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic.

The computer-readable medium described above may be further configured according to any of the embodiment(s) described herein. Each of the steps of the computer-implemented method executable by the program instructions may be further performed as described herein. In addition, the computer-implemented method executable by the program instructions may include any other step(s) of any other method(s) described herein.

An additional embodiment relates to a system configured to monitor a non-defect related characteristic of a patterned wafer. The system includes an inspection subsystem configured to generate output responsive to light from a patterned wafer. The system also includes a computer subsystem configured to determine differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic.

The embodiment of the system described above may be further configured according to any other embodiment(s) described herein. In addition, the embodiment of the system described above may be configured to perform any step(s) of any method embodiment(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
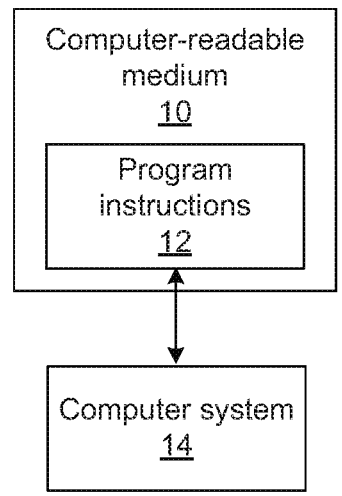
FIG. 1 is a block diagram illustrating one embodiment of a computer-readable medium that includes program instructions executable on a computer system for performing a computer-implemented method for monitoring a non-defect related characteristic of a patterned wafer.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits (ICs) may be formed on a wafer, and the term wafer as used herein is intended to encompass a wafer on which any type of device known in the art is being fabricated.

As used herein, the term "patterned wafer" is defined as a wafer having an uppermost layer or layers in which patterned features are formed. The patterned features may include any type of patterned features such as lines and spaces, contact holes or vias, and the like.

Although embodiments are described herein with respect to a patterned wafer, the embodiments described herein may be used for monitoring one or more non-defect related characteristics of any specimen that is fabricated using a process for which process monitoring and control based on the non-defect related characteristic(s) are desirable.

As used herein, the term "non-defect related characteristic" of a patterned wafer is generally defined as a characteristic of a patterned wafer that has a value that is normally measured using a metrology tool. In addition, although the non-defect related characteristic may have a value that if it is outside of some predetermined limit can render the wafer "defective," the non-defect related characteristic is not related to information about defects, as that term is commonly used in the art, that can be detected by an inspection system such as the presence of defects, the location of defects, the number of defects, etc. Examples of "non-defect related characteristics" of a patterned wafer include, but are not limited to, roughness of patterned feature(s) such as lines formed on the patterned wafer (i.e., line roughness or line edge roughness (LER)), critical dimension (CD) of patterned feature(s) formed on the patterned wafer, thickness of patterned feature(s) formed on the patterned wafer (e.g., line height), film or thin film thickness (e.g., thickness of a thin film such as oxide), step height of patterned feature(s) formed on the patterned wafer (e.g., silicon (Si) height), and profile of patterned features formed on the patterned wafer.

In general, the embodiments described herein are configured for using output generated by a patterned wafer inspection system to monitor a non-defect related characteristic of a patterned wafer. Methods and systems for determining a characteristic of a wafer using output generated by an inspection system are described in commonly owned U.S. patent application Ser. No. 11/673,150 by Kirk et al. filed Feb. 9, 2007, which published as U.S. Patent Application Publication No. 2008/0013083 on Jan. 17, 2008, and Ser. No. 11/751,970 by Chen et al. filed May 22, 2007, which published as U.S. Patent Application Publication No. 2008/0018887 on Jan. 24, 2008, all of which are incorporated by reference as if fully set forth herein.

Some methods and systems described in these patent applications have been implemented by using image data generated by unpatterned wafer inspection systems to monitor surface roughness of unpatterned wafers (e.g., the surface roughness of the uppermost unpatterned layer formed on the wafer). Such implementations are performed by assuming a correlation between surface roughness and the image data. The correlation coefficient is derived using empirical data. For example, a correlation coefficient from image data generated by an unpatterned wafer inspection system to surface roughness can be built in the field manually using wafers. When the assumption is not true, the approach reports the issue to the user.

However, due to the complexity of patterned wafers and different pattern designs that are formed on patterned wafers, the implementations described above cannot be used for patterned wafers with patterned wafer inspection systems. In particular, the relationship between a non-defect related characteristic (metrology) and raw intensity (or attributes) of image data generated by patterned wafer inspection systems is much more complicated and highly depends on the pattern formed on the wafer and the optics configuration of the inspection system that is used to generate the image data. As will become apparent based on the following description, the embodiments described herein are much more suitable for monitoring a non-defect related characteristic of a patterned wafer than previously used methods and systems.

The implementations described above also generally involve full wafer scanning in which the inspection system scans the entire unpatterned wafer with relatively low resolution to produce a gray level map of light scattered from the wafer. Such implementations are sensitive to a limited number of non-defect related characteristics (metrology variables) and measure the sum effect of all of them during the scan. Because the implementations do not discriminate any part of the die that would be formed on a patterned wafer and use the same optical parameters of the inspection system (e.g., band/mode recipe, i.e., a combination of the wavelength band and optical mode of the inspection system used for any one inspection recipe) across the whole wafer, the implementations cannot be sensitive to just a particular non-defect related characteristic (metrology variable) of a patterned wafer. In contrast, as described further herein, a particular patterned feature in a die and a set of particular parameters (e.g., a particular band/mode) of an inspection system can be selected and used to maximize the sensitivity of a scan to a single non-defect related characteristic (metrology variable) of a patterned wafer.

One embodiment relates to a computer-implemented method for monitoring a non-defect related characteristic of a patterned wafer. The method includes generating output responsive to light from a patterned wafer using an inspection system. The inspection system may be configured for patterned wafer inspection or only patterned wafer inspection. In this manner, the inspection system may be configured as a patterned wafer inspection system. Since the embodiments described herein are configured for monitoring a non-defect related characteristic of a patterned wafer, inspection systems configured for inspection of unpatterned wafers (e.g., a dark field (DF) laser scattering-based inspection system configured for unpatterned wafer inspection with rather low spatial resolution (e.g., about 50 µm) and much faster inspection of a whole wafer than patterned wafer inspection systems) will be generally unsuitable for use in the embodiments described herein.

In one embodiment, one or more parameters of the inspection system used for generating the output render the output unsuitable for use in detecting defects on the patterned wafer. For example, a recipe for wafer inspection is generally created by maximizing the signal-to-noise ratio (S/N) for defects of interest paying no attention to process variations across the wafer other than to minimize their impact on the robustness of the recipe across the wafer and across lot-to-lot inspections. As such, currently used methods for inspecting patterned wafers generally are set by the inspection recipe to not collect light that is responsive to process variations, which describe metrology changes across the patterned wafers, and do not attempt to emphasize sensitivity to such light and therefore such process variations. Therefore, one or more parameters of the inspection system that are used to inspect a wafer for defects may be unsuitable for generating output that is responsive to a non-defect related characteristic of the patterned wafer. In addition, one or more parameters of the inspection system that can be used to generate output that is responsive to a non-defect related characteristic of the patterned wafer may be unsuitable for generating output that is responsive to defects on the wafer. Therefore, in some instances, the embodiments described herein may be different than methods for detecting defects on a patterned wafer or inspecting a patterned wafer in that the one or more parameters of the inspection system used for the embodiments described herein may be different than one or more parameters of the inspection system that are used for inspection methods. In this manner, various changes in one or more non-defect related characteristics (various metrology changes) of a wafer can be sensed as described further herein using inspection systems when they are not used in normal inspection modes. Therefore, the embodiments described herein are almost the opposite to defect inspection in which process variations (metrology changes) are considered noise in detecting to defects, and many techniques were developed to ignore the process variations. The one or more parameters of the inspection system used in this embodiment may include any one or more optical parameters of the inspection system (e.g., wavelength(s) of illumination, wavelength(s) of collection/detection, angle(s) of illumination, angle(s) of collection/detection, polarization of illumination, polarization of collection/detection, and the like) and may be selected as described herein.

However, occasionally the inspection recipe can provide sensitivity to the non-defect metrology changes even if it was not specifically setup for that function. Therefore, in some instances, one or more parameters of the inspection system used for generating the output in the embodiments described herein may not render the output unsuitable for use in detecting defects on the patterned wafer. In other words, in some instances, the same output may be used for metrology variable monitoring and defect detection. In this manner, an existing inspection recipe may be used to generate the output in the embodiments described herein.

In another embodiment, one or more parameters of the inspection system used for generating the output are different than one or more parameters of the inspection system used to generate additional output for the patterned wafer, and the additional output can be used to detect defects on the patterned wafer. For example, as described above, one or more parameters of the inspection system that can be used to generate output that is responsive to the non-defect related characteristic of the patterned wafer may be unsuitable or sub-optimal for generating output to be used for detecting defects on the patterned wafer. Therefore, in some such instances, different output may be generated for the patterned wafer using one or more different parameters of the inspection system. In this manner, some of the output generated for the patterned wafer may be used to monitor the non-defect related characteristic of the patterned wafer, and other output generated for the patterned wafer may be used to detect defects on the patterned wafer. Different output may be generated for the wafer using one or more different parameters of the inspection system in different scans or passes of the wafer performed by the inspection system (with appropriate changes to the one or more parameters between scans). Alternatively, if output can be generated using one or more different parameters of the inspection system simultaneously, the output and the different output may be generated in the same pass or scan of the patterned wafer. Different output may also be generated using one or more different parameters of the inspection system in any other suitable manner. In addition, the one or more different parameters used to generate the output and the additional output may include any of the parameters described herein and may be selected as described herein.

In an additional embodiment, the method includes selecting one or more parameters of the inspection system to be used for generating the output based on information about patterned features formed on the patterned wafer, information about the inspection system, and the non-defect related characteristic. For example, various parameters (e.g., bands/modes) of an inspection system can be more or less sensitive to a change in a non-defect related characteristic, and the patterned features formed on a wafer will also affect which of the non-defect related characteristics (metrology variables) can be sensed by the inspection system. In one such example, if substantially dense patterns of lines cannot be resolved by a particular set of parameters of an inspection system, the output generated for the patterned wafer by the inspection system using that set of parameters may be responsive to only surface roughness of the lines and not information about the depth or width of the lines. In this manner, the best parameters of the inspection system (e.g., band/mode inspection recipe) for sensing a non-defect related characteristic (a metrology variable) may be selected as described herein. In addition, the best parameters (e.g., band/mode recipe(s)) that can be used for concurrent inspection and metrology may be selected as described herein. For example, if the output of the inspection system (e.g., image data) is to be used concurrently for scanning a wafer for defect inspection and monitoring one or more selected non-defect related characteristics (metrology variable(s)) of the wafer, the selection of a particular set of parameters (e.g., inspection band/mode) may be paramount in determining whether the non-defect related characteristic(s) (metrology variable(s)) will be sensed during the inspection scan. As described herein, the best one or more parameters (e.g., band/mode recipe) of the inspection system may be selected to accomplish the sensing of the non-defect related characteristic while maintaining the defect inspection sensitivity.

Since the embodiments described herein are configured for patterned wafers, the inspection systems used in the embodiments described herein are patterned wafer inspection systems. Such inspection systems generally have more parameters that are adjustable than inspection systems configured for unpatterned wafer inspection. For example, unpatterned wafer inspection systems generally do not have adjustable wavelengths and aperture conditions while inspection systems configured for patterned wafer inspection generally do. Therefore, using a patterned wafer inspection system in the embodiments described herein instead of an unpatterned wafer inspection system allows many more parameters to be used for generating the output and evaluation of many more relationships between one or more attributes of the output and values of the non-defect related characteristic of the patterned wafer, which can be used as described further herein to monitor the non-defect related characteristic.

A method for selecting the best one or more parameters (e.g., band/mode) of the inspection system for both inspection and metrology given the non-defect related characteristic (metrology variable) desired to be monitored may be performed using inputs that include information about the inspection system (e.g., bright field (BF) or DF inspection system), the inspection recipe, detailed knowledge of the layout of a die on the patterned wafer (e.g., information from a GDSII file), and the non-defect related characteristic(s) (metrology variable(s)) desired to be monitored. The non-defect related characteristic input may be used to determine attributes of patterned features from metrology. In addition, the inspection system information input (e.g., BF or DF inspection system) may be used to determine patterned feature attributes from inspection system type. For example, the patterned feature attributes from metrology and the patterned feature attributes from inspection system type may be determined as shown in Table 1, which includes metrology propagation mechanisms and how to sense them using an inspection system.

TABLE 1

| Metrology | Propagating Effect | Setup Considerations Minimize | Maximize | Wafer Location | Attribute |
|---|---|---|---|---|---|
| Line Roughness | Scatters light into 2π | No propagating specular or diffracted light. So, true DF where no pattern is seen in the image | Light enough to overcome tool noise, need relatively large pixel size, substantially polarization dependent | Array only | Mean intensity, no die-to-die subtraction |
| CD variation | Alters specular and diffracted light intensities | Effects of other metrology changes are similar, so probably broadband BF modes, relatively small pixel sizes to better resolve wafer structures | BF (or DF) where pattern is present in the image, polarization dependent | Resolved random logic | Mean intensity, no die-to-die subtraction |
| Thin film thickness (e.g., oxide) | Alters specular and diffracted light intensities through thin film interference effects | Broadband washes out the interference effects, some narrow band (NB) wavelengths better than others | Single color or NB BF or DF emphasizes any thin film interference effects, polarization insensitive mostly | Resolved random logic and dense arrays | Mean intensity, no die-to-die subtraction |
| Step height | Alters specular and diffracted light intensities through coherent scatter interference | Broadband might be preferred | BF (or DF) where pattern is present in the image, polarization dependent | Resolved random logic | Mean intensity, no die-to-die subtraction |

It is noted that other than line roughness, all of the non-defect related characteristics included in Table 1 affect specular and diffracted light in the same manner. Therefore, the mechanism (band/mode) that can be used to sense the change in the non-defect related characteristic will be substantially layer dependent and not at all obvious how to differentiate.

The knowledge of the layout of a die on the patterned wafer (e.g., information from a GDSII file) may be used with the patterned feature attributes from metrology (determined using the non-defect related characteristic input) and the patterned feature attributes from inspection system type (determined using the information about the inspection system) to filter cells in the layout of the die for the best match to the inspection system and non-defect related characteristic. For example, a GDSII file can be loaded into a code that identifies patterned features that are sized to scatter or diffract components of light into the inspection system numerical aperture (NA) of collection. If detailed knowledge of the layout of the die is not available, then a set of points of interest (POI) for metrology measurement can be used to define boundaries of the interesting die areas through region defining, which is described further herein. Once a die area has been identified that can best promote the sensing of the non-defect related characteristic in the die, the expected non-defect related characteristic variation can be combined with the cell layout.

A reticle field printed on the wafer may include multiple dies. In such instances, one or more areas within the overall reticle field that can best promote the sensing of the non-defect related characteristic may be identified as described above. The one or more areas within the reticle field that are identified may include one or more areas in only one die in the reticle field or one or more areas in multiple dies in the reticle field (which may include all or only some of the dies in the reticle field). In addition, a "die" as used herein is intended to include dies that are printed using single die reticles (and therefore have an area that is approximately equal to the area of the reticle field) and dies that are printed using multiple die reticles (and therefore have an area that is less than the area of the reticle field).

The patterned features identified as described above may be fed into an electromagnetic (EM) simulator that combines the non-defect related characteristic to be monitored into the patterned feature definition and simulates the inspection system response across its available parameters (e.g., bands/modes) and selects the best candidate parameters (e.g., band/modes) to setup the inspection recipe. For example, the patterned feature layer information along with expected variations in the non-defect related characteristic may be passed as input to an EM simulator (such as a rigorous coupled wave analysis (RCWA) or finite-difference time-domain (FDTD) simulator that solves Maxwell's equations). The EM simulator may be run on the selected die cell(s) in the layout of the die (or the layout of a reticle field) to find the far-field amplitude and phase resulting from the metrology modified wafer structures. The results of running the EM simulator and the information about the inspection system may be used to process the EM files for the inspection system. For example, the amplitude and phase files may be combined with the desired inspection system to output the possible signals as a function of the available parameters (e.g., bands/modes) of the inspection system. In this manner, unlike implementations of using an inspection system to monitor a non-defect related characteristic of a wafer that use the same band/mode recipe across the whole wafer and therefore cannot be sensitive to just a particular non-defect related characteristic of a patterned wafer, the embodiments described herein can select a particular parameter or parameters of the inspection system to maximize the sensitivity of a scan to a single non-defect related characteristic of the patterned wafer.

The processed EM files for the inspection system may be used with the inspection recipe to select the parameters that combine inspection and metrology and to select the image attribute to collect using the output (e.g., the image of the patterned wafer) generated by the inspection system. For example, a final step may be to combine the defect inspection recipe with the metrology recipe to find the optimum recipe that is sensitive to the attribute of the image data for the patterned wafer generated by the inspection system (e.g., a frame image metric such as maximum, mean, range, etc.

of intensity) that is most likely to be the best to illustrate the variation of the non-defect related characteristic. The process of simulation may be performed on multiple cells in the die (or multiple cells in multiple dies in a reticle field) to determine the best cell (in the die or in the reticle field) that can be used to differentiate the non-defect related characteristic variation as well as to combine the metrology recipe for the cell with the inspection recipe. The output may include a pareto of inspection system parameters (e.g., band/modes) for inspection and monitoring the non-defect related characteristic of the patterned wafer.

In this manner, the method may include optimizing the recipe to be used for inspection and monitoring the non-defect related characteristic of the patterned wafer. For example, the selection of the best concurrent inspection and metrology recipe may be performed by calculating the simulation output for the signals developed from each parameter (e.g., band/mode) of the inspection system in terms of a figure of merit (FoM). This FoM may include factors that combine the signal for each purpose and include the S/N for the defect inspection and the signals for the metrology function. A similar algorithm has been developed for finding the best defect signal and defect S/N for applications in which adequate signal and enough S/N are needed in order for a defect to be detected. The FoM can weight each factor and output the best combination. In this manner, the one or more parameters of the inspection system used for generating the output may be selected such that inspection and monitoring the non-defect related characteristic can be performed using output generated in the same process (if not in the same scan) thereby adding significantly to the inspection results for defects by including a measure of the process variation and metrology variation.

Although the same output generated by the inspection system may be used to both inspect the patterned wafer for defects and to monitor a non-defect related characteristic of the patterned wafer, the output may be processed differently, than as in a recipe for inspection only, to both detect defects on the wafer and to monitor the non-defect related characteristic. For example, using current inspection recipes, the same output can be used for both inspection and metrology if the same attribute of the output that is used for inspection (e.g., usually maximum difference of the images) is also used for metrology. However, in such processing, spatial information would be lost for metrology since each image data frame is a significant part of the whole camera image size for which only one attribute result is typically reported for the metrology. For example, if there are 50 defects in a frame, the inspection system would report all of the defects with information about their location, but if the single attribute were the maximum difference for that frame, the only metrology output would be the signal from the brightest defect and that would be assigned to the frame area of the wafer associated with the frame size. As such, only that attribute would be available for use in the embodiments described herein. Therefore, in embodiments described herein in which defects are detected on the wafer and a non-defect related characteristic is monitored using the same output, the same output may be separately processed, once to detect defects on the wafer and again to monitor the non-defect related characteristic. Such processing may be performed by the same computer system, by different computer systems, or in any other suitable manner.

In one embodiment, generating the output is performed for only one or more sets of selected areas on the patterned wafer. For example, as described further herein, the non-defect related characteristic may be monitored at only one or more sets of selected areas on the patterned wafer. In this manner, there may be no need to generate the output across the entire wafer, particularly if the output is not also going to be used to detect defects on the wafer. Generating the output at only the one or more sets of selected areas on the patterned wafer may be performed in any suitable manner by the inspection system. The one or more sets of areas may be selected as described further herein.

In some embodiments, the output is responsive to light scattered from the patterned wafer, and generating the output does not involve Fourier filtering. For example, since the output is used as described herein to determine differences between a value of a non-defect related characteristic of the patterned wafer and a known value, the output is preferably responsive to light scattered from patterned features formed on the patterned wafer particularly if the non-defect related characteristic is a non-defect related characteristic of the patterned features formed on the patterned wafer, which may most often be the case. However, if Fourier filtering is performed on the light scattered from the wafer (e.g., by optical Fourier filtering) to remove the light diffracted from a repetitive structure or the output generated by the inspection system responsive to the scattered light (e.g., by electronic Fourier filtering), then the output responsive to the light scattered from the patterned features will be substantially eliminated. Therefore, Fourier filtering would eliminate important information about the patterned features from the output for the patterned wafer. As such, Fourier filtering may not be applied during generating the output (e.g., optically) or to the generated output (e.g., electronically) to maintain the scattering from the patterned features.

The method also includes determining differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic. For example, by using output of an inspection system that would generally be considered noise in inspection applications, it has been discovered that this noise may actually be proportional to various changes in non-defect related characteristics (metrology changes) across the patterned wafer. In this manner, the method may include extracting metrology information such as changes in non-defect related characteristic(s) from a raw image of the patterned wafer and/or image data generated for the patterned wafer by the inspection system. In particular, determining the differences as described above may include extracting changes in a value of the non-defect related characteristic relative to a known value (a baseline). The baseline may be established as described further herein using absolute metrology values. Therefore, by exploring the capability of an inspection system for patterned wafer metrology compared to the traditional understanding of the system for defect detection, new metrology applications have been opened up for the inspection system.

Since the differences between the value of the non-defect related characteristic and the known value are determined in the embodiments described herein, the differences are a measure of the process variation and metrology variation across a wafer and across wafer lots. In this manner, by determining the differences between the value of the non-defect related characteristic of the patterned wafer and a known value, the embodiments described herein effectively monitor changes in the value of the non-defect related characteristic of the patterned wafer compared to the known value. For example, the embodiments described herein can be used for monitoring changes in subsequently tested patterned wafers from an original calibration and correlation, not necessarily for determining the absolute magnitude of the non-defect related characteristic. Therefore, the embodiments described herein could be used as a form of process control in which patterned wafers are sampled to see if the process has wandered to produce an undesirable result.

In one embodiment, the output and the other output include image data. In this manner, the embodiments described herein may be performed using image data or images of the patterned wafer generated by an inspection system (inspection images). The one or more attributes of the output and the other output may be raw intensity values of the image data or images. One or more attributes of the image data can also be extracted from the image and plotted to generate other images for the patterned wafer. In addition, there are several possible attributes of image data that can be used in the embodiments described herein such as, but not limited to, the range of the intensity values, the maximum intensity value, and the median of the intensity values. In addition, the image data may be difference image data, which can be generated by subtracting the image of one die on the patterned wafer from the image of another die on the patterned wafer (e.g., an adjacent die) or one cell to another adjacent cell within the same die. One or more attributes of the difference image data that may be used in the embodiments described herein may include, for example, range of the image intensity values, mean variation, and maximum. In this manner, in some embodiments, the one or more attributes of the output and the other output includes one or more statistical attributes (e.g., mean of the intensity values of the image data, mean variation of the difference image data, average raw intensity, etc.). There are literally dozens of possible attributes that could be extracted from the image data generated by the inspection system and used in the embodiments described herein. Therefore, the embodiments described herein may use images generated by inspection systems to serve metrology use cases.

Since the embodiments described herein are intended for use for patterned wafers, the embodiments will generally be performed using a patterned wafer inspection system as opposed to an unpatterned wafer inspection system. Many more attributes can be extracted from the output generated by patterned wafer inspection systems than from the output generated by unpatterned wafer inspection systems. For example, unpatterned wafer inspection systems are generally not capable of performing die-to-die or cell-to-cell comparisons, particularly if they are configured to scan the wafer while rotating the wafer. As such, one or more attributes of difference image data would typically not be available for use in the embodiments described herein if the embodiments were performed using an unpatterned wafer inspected system. Therefore, by using a patterned wafer inspection system in the embodiments described herein, many more attributes of the output will be available for use in the embodiments described herein. Having more attributes available for use in the embodiments described herein may be advantageous because the attributes of the output that are most sensitive to the non-defect related characteristic of interest can be identified and used in the embodiments described herein.

Furthermore, since patterned wafer inspection systems typically have much higher spatial resolution than unpatterned wafer inspection systems, the one or more attributes can be determined for the image data with much higher spatial resolution across the wafer when the embodiments are performed using a patterned wafer inspection system rather than an unpatterned wafer inspection system. For example, patterned wafer inspection systems typically perform much higher spatial sampling of patterned wafers compared to the spatial sampling performed by unpatterned wafer inspection systems for unpatterned wafers. In one such example, patterned wafer inspection systems may have a spatial sampling of about 0.1 μm to about 2 μm and a pixel size of about 50 nm to about 250 nm or so. Therefore, even if a frame of image data (e.g., about 512 pixels by about 512 pixels) is processed collectively to determine one or more attributes of the image data, the one or more attributes will be determined with relatively high resolution. As such, the resolution with which the one or more attributes can be determined renders the output generated by a patterned wafer inspection system much more suitable for use in the embodiments described herein than the output typically generated by unpatterned wafer inspection systems.

In another embodiment, determining the differences is performed for only one or more sets of selected areas on the patterned wafer based on the differences between the one or more attributes of the output generated for only the one or more sets of selected areas on the patterned wafer and the one or more attributes of the other output for only one or more corresponding sets of selected areas on the different patterned wafer. For example, the one or more sets of selected areas may include only one discrete area in each die on the wafer (or only one discrete area in a multiple die reticle field) since the metrology can be generally considered unchanged within a die (and within a reticle field). In addition, currently performed metrology processes generally use a metrology sampling concept in which a particular structure printed on a wafer, usually in a street between dies, is used to measure a metrology variable at anywhere between about 9 and maybe 50 locations across the whole wafer and from that deduce what might be happening over the whole wafer (e.g., in the dies on the wafer). However, the embodiments described herein can be performed for only one or more sets of selected areas in the die or dies printed on the wafer where the metrology actually matters. In addition, since the embodiments described herein are configured for patterned wafers, the inspection system used by the embodiments described herein will generally be a patterned wafer inspection system. As such, unlike unpatterned wafer inspection systems that are generally incapable of performing measurements or inspection of a wafer at only selected locations, the embodiments described herein can be performed by sampling only a particular portion of a die or a reticle field.

In addition, although the method may be performed for only one or more sets of selected areas on the patterned wafer, the output may be generated across substantially the whole patterned wafer (e.g., if the entire patterned wafer is scanned by the inspection system). Therefore, the embodiments described herein may sample the patterned wafer in the actual die or the actual field at a sampling scale of the frame of the image (which might be about 50 nm to about 500 nm) over the whole wafer and report the overall result. Therefore, the embodiments described herein can monitor a non-defect related characteristic of a patterned wafer at substantially high resolution across the entire wafer.

In an additional embodiment, the method includes selecting one or more sets of areas on the patterned wafer, and the determining step is performed for only the one or more sets of selected areas on the patterned wafer based on the differences between the one or more attributes of the output generated for only the one or more sets of selected areas on the patterned wafer and the one or more attributes of the other output for only one or more corresponding sets of selected areas on the different patterned wafer. In this manner, the method may include care area selection for patterned wafer metrology (e.g., wafer-scale metrology). The selection of a particular part of the die printed on the wafer or a particular part of a reticle field printed on the wafer for which the method is performed may be paramount in determining whether the non-defect related characteristic (metrology variable) can be sensed (e.g., during the inspection scan). As described herein, a particular part of the die or the reticle field can be identified such that a non-defect related characteristic (metrology variable) can be sensed during the inspection. In addition, a part of a die or a reticle field that is best for sensing a non-defect related characteristic (metrology variable) can be selected as described herein.

The one or more sets of areas on the wafer may be selected to include a particular patterned feature on the patterned wafer. For example, the non-defect related characteristic variation that is desired to be sensed during the inspection determines the type of patterned features that can best be used by an inspection system to be sensitive to that particular variation. The main feature in such a determination is which optical mechanism propagates changes in the non-defect related characteristic to the inspection system. For example, the inspection system may have a particular collection aperture located in the far-field from the patterned wafer where only certain parts of the light leaving the wafer can be collected by the inspection system. In one such example, a BF inspection system may collect a maximum of about 64 degrees from the vertical (equivalent to an NA of about 0.90). Therefore, light leaving the patterned wafer with an angle greater than about 64 degrees from the vertical will not be sensed by the inspection system. The light leaving the patterned wafer may be in the form of scattered light, specularly reflected light, and diffracted light. Each of these mechanisms can relay information about the patterned features formed on the patterned wafer and changes in the non-defect related characteristic of the patterned features. How they propagate depends on the layout of the patterned features and the type of non-defect related characteristic. Table 1 shows how to separate the non-defect related characteristic into the three types of propagating mechanisms and which might be sensed by a particular recipe used for monitoring the non-defect related characteristic of the patterned wafer. In this manner, unlike implementations of using an inspection system to determine a non-defect related characteristic of a wafer that do not discriminate any part of the die or reticle field and therefore cannot be sensitive to just one particular non-defect related characteristic or may not be sensitive to any non-defect related characteristics, the embodiments described herein show how a particular patterned feature in a die or reticle field can be used to maximize the sensitivity of a scan to a single non-defect related characteristic.

When information about the patterned features formed on the patterned wafer (e.g., a GDSII die file) is not available, then a set of user selected metrology POI can be passed into a code. When an inspection system (e.g., a DF inspection system) scans the wafer, the images generated at these POI wafer coordinates may be processed by region defining to automatically define the rectangular boundary of the metrology region, and differences in the value of the non-defect related characteristic corresponding to the regions can be determined.

Two different approaches may be used for defining a set of die areas or reticle field areas to be used for monitoring the non-defect related characteristic. In general, the different approaches define region boundaries from a set of user selected POIs for further non-defect related characteristic monitoring. In one approach, a user may define a set of POIs using zoomed optical images within one die or one field. During the setup, the inspection system may scan the POI sites and a region defining step (which may be performed using a region defining algorithm) may determine the exact rectangular boundaries (RB) for the regions containing the POIs. During the method, the RBs of one die or field may be replicated for all dies or fields and be sent to code along with the output (e.g., image) to be used for determining the differences between the value of the non-defect related characteristic and the known value. In another approach, a user may define a set of POIs or obtain the metrology points for the entire wafer. During a scan (e.g., an inspection scan), the POI locations may be sent to the code. Region defining (which may be performed using a region defining algorithm) may determine the region of interest (ROI) boundary on-the-fly and determine the differences between the value of the non-defect related characteristic and the known value for the regions whose boundaries are defined.

Both of the above-described approaches can automatically define interesting die or reticle field areas from a set of starting points, and yet they are aimed at slightly different applications. The first approach defines the region at setup stage for one die or one field. The regions can be replicated to all dies or all fields. Therefore, it is suitable for image acquisition for a specific metrology area on all die or all fields. The second approach, however, allows different metrology points on different die or different fields on a patterned wafer, and it saves the effort of setup. Determining the differences between the value and the known value can be performed on-the-fly.

In one such embodiment, all patterned features formed in the one or more sets of selected areas have substantially the same characteristics. For example, all patterned features formed in the one or more sets of selected areas may have substantially the same pitch, substantially the same dimensions such as line width and height, substantially the same shape, substantially the same profile, etc. In addition, although some of the patterned features formed in the one or more sets of selected areas may have one or more characteristics that are somewhat different (e.g., due to defects on the patterned wafer and/or variations in the characteristics due to marginalities in the process or processes used to form the patterned features), the patterned features formed in the one or more sets of selected areas may be designed to have the same characteristics.

In one embodiment in which all patterned features formed in the one or more sets of selected areas have substantially the same characteristics, region defining (which may be performed by a region defining algorithm) may include the following steps. Starting from a user selected point inside a ROI, a patterned feature characteristic may be collected horizontally and vertically across an entire frame surrounding the point. The horizontal and vertical boundaries may be determined based on homogeneity of the patterned feature characteristic collected horizontally and vertically. The vertical and horizontal region boundaries may then be combined based on the determined horizontal and vertical boundaries.

As described above, the method may include selecting one or more parameters of the inspection system to be used for generating the output. In addition, the method may include selecting one or more sets of areas on the patterned wafer for which the differences are determined. Since as described above, the one or more parameters of the inspection system that are suitable for generating the output may vary depending on the patterned features for which the differences are determined, the method may include selecting the one or more sets of areas and selecting the one or more parameters of the inspection system based on the selected one or more sets of areas.

There are a number of possible methods that can be used to select the part of the die or reticle field and the one or more parameters (e.g., band/mode) of the inspection system that will be sensitive to a particular non-defect related characteristic. For example, one method may include brute force imaging of at least a die row or field row across a wafer that has a known variation in a set of non-defect related characteristics with an image correlation by region to the non-defect related characteristic. Here, an image of each part of the die or field across the wafer is correlated to the non-defect related characteristic to determine the best fit. The correlation can be performed by solving a series of linear equations for each non-defect related characteristic and the image metric chosen. However, there are a multitude of possible inspection system parameters (e.g., band/modes), making this a potentially long process that is repeated with each combination of parameters (e.g., band and mode) until the best combination is identified.

In one embodiment, determining the differences is performed based on a correlation between the differences between the one or more attributes of the output and the one or more attributes of the other output and the differences between the value and the known value. For example, there may be a correlation between differences in the image data generated for the patterned wafer and the different patterned wafer and differences in the value of the non-defect related characteristic and the known value if the image date depends on only one major non-defect related characteristic. In other words, in the idealized case, if there is only one major non-defect related characteristic, then the observed one or more attributes of the image data will be correlated to the change in the non-defect related characteristic. In one such example, a correlation between the image data generated for the patterned wafer by the inspection system and metrology may exist if the scattering is mainly responsive to only a change in a single non-defect related characteristic of the patterned wafer. For example, for an optics mode that is sensitive mainly to only one non-defect related characteristic, the image data for the patterned wafer may correlate with the metrology measurement. In one particular example, changes in image data responsive to light scattered from a patterned wafer generated using an optics mode, which can be generally defined by oblique incidence, p-polarized illumination, and unpolarized detection, of the Puma inspection system, which is commercially available from KLA-Tencor, San Jose, Calif., visually appeared to exhibit a correlation with changes in step height of patterned features formed on the patterned wafer measured using a metrology system. However, in reality, several non-defect related characteristics can be changing across the wafer at once. Different attributes of the image data can be more or less sensitive to these non-defect related characteristics and also where they occur on the wafer and in what patterned features. As such, if an attribute of the image data is found that just happens to be sensitive to one single non-defect related characteristic and insensitive to others, then the other non-defect related characteristics can be ignored. In this manner, any contribution from other non-defect related characteristics to the attribute(s) of the image data can be ignored.

Many inspection systems will, however, be sensitive to a combination of changes in various non-defect related characteristics that can interfere, and it may not be particularly easy to separate out the change in the non-defect related characteristic that the user is interested in. Therefore, in another embodiment, determining the differences is performed based on a correlation between the differences between the one or more attributes of the output and the one or more attributes of the other output and a linear combination of the differences between the value and the known value and differences between a value of at least one other non-defect related characteristic of the patterned wafer and a known value of the at least one other non-defect related characteristic of the different patterned wafer. For example, from a signal formation hypothesis point of view, for a given patterned feature, the scattering response change may be approximately a linear combination of metrology changes. In one such example, by focusing on the relationship between an image of a wafer generated by an inspection system and the raw intensity value of the inspection image, it has been discovered that changes in the raw intensity value for a patterned wafer (from a raw intensity value for a different patterned wafer having known values of two or more non-defect related characteristics) can be estimated by a linear combination of changes in the two or more non-defect related characteristics. In this manner, metrology changes can be measured across a wafer, and then a correlation can be performed to the observed attributes of the image data across various parameters of the inspection system (e.g., bands/modes) to arrive at a way of separating the metrology variables from the image data. Therefore, if a particular set of parameters of the inspection system that is sensitive to only the non-defect related characteristic of interest cannot be identified, a linear combination of changes in two or more non-defect related characteristics may be used to determine the differences in the non-defect related characteristic.

This relationship has been validated from a perturbation theory point of view. For example, a scattering response change may be the linear combination of metrology variable changes if the metrology change is relatively small. In particular, let S be the mean scattering response for a specific pattern, and $M_i$ be the metrology variables on the wafer, then perturbation theory tells us:

$$S = f(M_1, M_2, \ldots, M_n)$$

$$\Delta S = f(M_1 + \Delta M_1, M_2 + \Delta M_2, \ldots, M_n + \Delta M_n) - f(M_1, M_2, \ldots, M_n) =$$

$$\frac{\partial f}{\partial M_1}\bigg|M_1, M_2, \ldots, M_n \Delta M_1 + \frac{\partial f}{\partial M_2}\bigg|M_1,$$

$$M_2, \ldots, M_n \Delta M_2 + \ldots + \frac{\partial f}{\partial M_n}\bigg|M_1, M_2, \ldots,$$

$$M_n \Delta M_n + O((\Delta M_1)^{l_1}(\Delta M_2)^{l_2} \ldots (\Delta M_n)^{l_n})$$

For $$l_1 + l_2 + \ldots + l_n >= 2,$$

provided $\dfrac{\partial^{k_1 + k_2 + \ldots + k_n} f}{\partial M_1^{k_1} \partial M_2^{k_2} \ldots \partial M_n^{k_n}}$ exists for $k_1, k_2, \ldots, k_n >= 0$.

If $O((\Delta M_1)^{l_1}(\Delta M_2)^{l_2} \ldots (\Delta M_n)^{l_n}) \to 0$ when $\Delta M_i \to 0$, we have $\Delta S = a_1 \Delta M_1 + a_2 \Delta M_2 + \ldots + a_n \Delta M_n$.

The linear hypothesis from perturbation theory should be true for every point measured on a wafer. In addition, the linear hypothesis from perturbation theory should be true for mean scattering in a relatively small area if local variation in the non-defect related characteristics can be ignored within the area. Therefore, the linear hypothesis should be true for the embodiments described herein. In particular, the embodiments may generally be performed for only sets of selected areas on the wafer that have substantially the same patterned features formed therein and that are typically substantially small (e.g., typically less than about 100 µm) relative to the whole wafer (e.g., which may have a diameter of about 300 mm). In addition, non-defect related characteristics tend to change relatively slowly across a wafer and vary across the whole wafer in some low order curve. Therefore, any change in metrology over a few 100 µm is basically zero.

In addition, the metrology variables should not change much unless there is a deliberately induced change like a stepper exposure or focus change where the whole reticle field will change relative to its neighbor reticle fields (these may typically include several die that are all basically the same within the reticle field). For example, sometimes a fab will expose a wafer in a focus-exposure matrix layout in which exposure is varied along one direction on the wafer while focus is varied along the opposite direction on the wafer. In this manner, each of the reticle fields is printed on the wafer at a different combination of focus and exposure values. For such wafers, the linear hypothesis described above should also be true for a whole reticle field because the non-defect related characteristics within the whole reticle field should be substantially constant.

The perturbation theory hypothesis described above can be expanded to evaluate the change in light scattered from a patterned wafer along a direction on the wafer in which different dies are printed with different exposure conditions. In this manner, the scatter change is evaluated along the exposure change direction. In addition, mean scatter change can be used in this evaluation although other attributes of the scattering may be responsive to interesting property or properties related to metrology as well. In this evaluation, the care area is defined to contain a single pattern/structure, and Fourier filtering is not applied to maintain the scattering from the patterned features. Since one or more characteristics of the patterned features will change along the exposure change direction due to differences in the exposure conditions, this evaluation can be used to examine the relationship between differences in one or more attributes of the output and differences in one or more non-defect related characteristics of the patterned features.

In particular, from a signal formation hypothesis point of view, the signal formation is a linear combination of changes in non-defect related characteristics. Let S be the scattering response at location (x,y) in a die or a field on the patterned wafer, and $M_i(x,y)$ be the non-defect related characteristics (metrology variables) at the location, then $$S(x,y) = f(M_1(x,y), M_2(x,y), \ldots, M(x,y))$$

If only metrology changes at location (x,y), perturbation theory tells us that $$\Delta S(x, y) = f(M_1(x, y) + \Delta M_1(x, y),$$

$$M_2(x, y) + \Delta M_2(x, y), \ldots, M_n(x, y) + \Delta M_n(x, y)) -$$

-continued $$f(M_1(x,y), M_2(x,y), \ldots, M_n(x,y)) = \frac{\partial f}{\partial M_1}\bigg|M_1(x,y),$$

$$M_2(x,y), \ldots, M_n(x,y)\Delta M_1(x,y) + \frac{\partial f}{\partial M_2}\bigg|M_1(x,y),$$

$$M_2(x,y), \ldots,$$

$$M_n(x,y)\Delta M_2(x,y) + \ldots + \frac{\partial f}{\partial M_n}\bigg|M_1(x,y),$$

$$M_2(x,y), \ldots,$$

$$M_n(x,y)\Delta M_n(x,y) + O((\Delta M_1)^{l_1}(\Delta M_2)^{l_2} \ldots (\Delta M_n)^{l_n})$$

For $l_1 + l_2 + \ldots + l_n >= 2$, provided $\dfrac{\partial^{k_1+k_2+\ldots+k_n} f}{\partial M_1^{k_1} \partial M_2^{k_2} \ldots \partial M_n^{k_n}}$ exists for $k_1, k_2, \ldots, k_n >= 0$ Therefore, assuming that the structure at (x,y) and its neighborhood remains unchanged, the scatter change at each die location (x,y) (or reticle field location) is the linear combination of metrology changes at the location according to the following equation:

$$\Delta S(x,y) = a_1(x,y)\Delta M_1(x,y) + a_2(x,y)\Delta M_2(x,y) + \ldots + a_n(x,y)\Delta M_n(x,y)$$

From a signal hypothesis point of view for a patterned wafer that is exposed as described above with different exposure conditions from die to die (or field to field) along an exposure direction on the patterned wafer, at the die or field location (x,y), the patterned feature(s) remain the same and only the non-defect related characteristic of the patterned features changes (i.e., the metrology changes) from die to die (or field to field). The scatter change from die to die (or field to field), therefore, should be the linear combination of the changes in the non-defect related characteristics from die to die (or field to field).

For the mean scatter in a neighborhood, within a neighborhood of a location at (x,y), assume the metrology change from die to die (or field to field) is constant, i.e., for any two points $(x_1,y_1)$, $(x_2,y_2)$ in the neighborhood of (x,y), we have $$\Delta M_i(x_1,y_1) = \Delta M_i(x_2,y_2).$$

Then, the mean scatter in the neighborhood of (x,y) is $$\overline{\Delta S} = \frac{\iint \Delta S(x,y)dxdy}{\iint dxdy} =$$

$$\frac{\iint a_1(x,y)\Delta M_1(x,y)}{\iint dxdy}dxdy + \frac{\iint a_2(x,y)\Delta M_2(x,y)}{\iint dxdy}dxdy +$$

$$\ldots + \frac{\iint a_n(x,y)\Delta M_n(x,y)}{\iint dxdy}dxdy = \frac{\iint a_1(x,y)}{\iint dxdy}dxdy\Delta M_1 +$$

$$\frac{\iint a_2(x,y)}{\iint dxdy}dxdy\Delta M_2 + \ldots + \frac{\iint a_n(x,y)}{\iint dxdy}dxdy\Delta M_n$$

Therefore, from die to die (or field to field), the mean scatter change in a relatively small area is a linear combination of the changes in the non-defect related characteristics within the area as defined by the following equation:

$$\overline{\Delta S} = \overline{a_1}\Delta M_1 + \overline{a_2}\Delta M_2 + \ldots + \overline{a_n}\Delta M_n.$$

Therefore, by looking at a sample of the wafer at each die or reticle field in which the non-defect related characteristics have been measured and has a particular set of non-defect related characteristics at that location, the observed signal or attribute of the output at that location is the linear combination of the effects of the non-defect related characteristics at that location.

The relationship has also been validated from real image data acquired using commercially available inspection systems including the 28xx and Puma systems that are available from KLA-Tencor. For example, the scattering response was measured for ladder patterns having different values of one or more non-defect related characteristics formed on a wafer. The scattering response measured from the wafer appeared to be a somewhat linear combination of changes in step height and line width of the ladder pattern.

The ladder pattern was not resolved in both the x and y directions by the inspection system. The metrology data used in the process was step height, line width in x and y directions, and LER. Film thickness and profile are assumed to have a relatively small effect on the scattering response and were therefore not measured by metrology. If there was not metrology data measured for an exact location evaluated on the patterned wafer, the interpolated surface generated by MASA software was used to extract the metrology data for that location (an algorithm that fits the data to a function where interpolation can be accomplished). The output generated by the inspection system used for the linearity validation was stored output, which was generated using two different optical modes, one that can generally be defined by oblique incidence illumination, p-polarized illumination, and unpolarized collection and another that can generally be defined by oblique incidence illumination, s-polarized illumination, and unpolarized collected. In addition, the output used for the linearity validation included output generated for only three care areas on the patterned wafer. Only a subset of the output generated for the wafer was used to validate the linearity because when using oblique incidence illumination the detectors of the inspection system were saturated due to region definition change. The non-defect related characteristics considered for the ladder pattern included Si height, film thickness, LER, and line width. Profile of the ladder pattern is relatively hard to measure, and because the ladder pattern is also relatively small, the profile of the ladder pattern was ignored.

To verify whether scattering is a linear combination of changes in non-defect related characteristics, assume $$\Delta mI = \alpha_1 \Delta SH + \alpha_2 \Delta LW_x + \alpha_3 \Delta LWy + \alpha_4 \Delta LER$$

$$\Delta mI = [\Delta SH, \Delta LWx, \Delta LWy, \Delta LER]\begin{bmatrix}\alpha_1\\\alpha_2\\\alpha_3\\\alpha_4\end{bmatrix}$$

$$[\Delta mI] = [\Delta \text{Metrology}]\begin{bmatrix}\alpha_1\\\alpha_2\\\alpha_3\\\alpha_4\end{bmatrix}$$

The mean intensity value of the light scattered from each different design pattern was determined from the stored output. For example, the array region was manually selected from an overall wafer image that was stored in a system such as that described in commonly owned U.S. patent application Ser. No. 12/234,201 by Bhaskar et al. filed Sep. 19, 2008, now U.S. Pat. No. 8,126,255 issued on Feb. 28, 2012, which is incorporated by reference as if fully set forth herein. Such a system may be commonly referred to as a virtual inspector (VI). A VI may generally be configured to acquire a wafer image from an inspection system as the wafer is being scanned and to store the wafer image on a disk storage array such that algorithms can be applied to and/or methods can be performed on the stored image at a later time. The attributes (statistics) of the output were then determined (mean in this case) from that small array region and may be compared to the attributes for the next die over which has the same structure. Metrology data was also obtained. In particular, the obtained metrology data included metrology data measured at the exact location and metrology data generated by using MASA software to perform interpolation/extrapolation and to then determine the projected values. A least square was used to find the linear coefficients $\hat{a}_1, \ldots, \hat{a}_n$.

$$(\hat{a}_1, \ldots, \hat{a}_n) = \min \|\overline{\Delta S} - (\overline{a_1}\Delta M_1 + \overline{a_2}\Delta M_2 + \ldots + \overline{a_n}\Delta M_n)\|$$

The error between mean intensity and linearly combined step height, line width, etc. was then evaluated. In this manner, the contribution to the scattered light from the non-defect related characteristics can be matched with the linear combination of the metrology data. Although validating the linearity of the relationship between the output and the non-defect related characteristics and determining the linear coefficients has been described above with respect to scattered light, validating the linearity and determining the linear coefficients can be performed in a similar manner for output that is responsive to light reflected from the patterned wafer (e.g., using image mean, line width in the x direction, line width in the y direction, LER, and step height). In essence, therefore, determining the linear coefficients can be viewed as a calibration stage of a process for monitoring a non-defect related characteristic of a patterned wafer. In addition, the linear coefficients can be determined for different parameters (e.g., optics modes) of the inspection system (i.e., different sets of one or more parameters of the inspection systems).

In this manner, if the linear coefficients are known, the changes in the non-defect related characteristics can be extracted from the raw intensity changes. In particular, if the linear coefficients are known and the number of non-defect related characteristics contributing to the scattering response is known, the changes in the non-defect related characteristics may be extracted by solving linear equations. In addition, even if multiple non-defect related characteristic changes are determined using a linear combination, the method may include reporting fewer than all of the non-defect related characteristic changes that are determined. For example, the user may be interested in only a single non-defect related characteristic and totally uninterested in others. In one such example, the user might be interested in monitoring the width of printed lines (e.g., CD) and not care about the thickness of the wafer or a layer on the wafer or roughness of the lines. However, if, due to the interdependence of non-defect related characteristics, a linear combination of changes in the non-defect related characteristics is used to determine the differences in the width of the printed lines, the changes in the width of the printed lines and the changes in the thickness of the layer may both need to be determined in order to determine the changes in the width of the printed lines although only the width of the printed lines may be reported to the user. For example, a calibration of a linear combination of changes in non-defect related characteristics with one or more observed attributes of the output may be performed to arrive at a recipe that is basically only sensitive to changes in the line widths. The user can then use that recipe to determine if the line widths have gone out of specification.

The linear coefficients are functions of patterned features (pattern/structure) and parameters of the inspection system (e.g., optics mode). Therefore, the linear equation is true for a specific pattern only. As such, single pattern care area definition may be key to the success of this operation. Such single pattern care areas can be selected as described further herein. In addition, single pattern care area definition should not be an issue. In particular, most of the time, region definition should be able to include a single pattern in the region. Furthermore, differences in one or more non-defect related characteristics of the patterned features such as pitch can have different relationships with differences in the one or more attributes of the output. Therefore, single pattern care area selection may also preferably involve selecting a single pattern that has substantially the same one or more characteristics, which may be performed as described above.

The linear coefficients can be determined in a number of different ways. For example, the linear coefficients can be determined by using a known wafer (i.e., a different patterned wafer having known values of non-defect related characteristics). In particular, if the metrology information $\Delta M_i$ is known from the wafer, $a_i$ can be determined. For example, $\Delta S$ can be determined from image data for the known wafer, $\Delta M_i$ can be determined from measured metrology performed for the known wafer, and then the following equation can be solved for $a_i$ $$(a_1, \ldots, a_n) = \min_{(a_1,\ldots,a_n)} (\|\Delta S - (a_1\Delta M_1 + a_2\Delta M_2 + \ldots + a_n\Delta M_n)\|).$$

Alternatively or additionally, the linear coefficients can be estimated from simulation. For example, by changing one non-defect related characteristic (metrology variable) at a time, making all other $\Delta M$ zero in the linear equation $$\Delta S = a_1\Delta M_1 + a_2\Delta M_2 + \ldots + a_n\Delta M_n$$

$a_i$ can be determined through the ratio of simulated response and non-defect related characteristic change input to the simulation.

$$a_i = \frac{\Delta S}{\Delta M_i}$$

Extraction of the changes in the non-defect related characteristics from the scattering response may then be performed using the following general mathematical approach. If n metrology terms are contributing to the scattering response, at least n linearly independent equations are needed to solve all n terms. For each set of one or more parameters used to scan the wafer, there is one equation. Assume there are N optics modes. At a certain location on the wafer, the responses are $$\Delta s^1, \Delta s^2, \ldots, \Delta s^N$$

These responses are obtained using the image data generated for the wafer by the inspection system. At the location, the non-defect related characteristics (metrology values) $\Delta m^1, \Delta m^2, \ldots, \Delta m^N$ may be determined through equations $$\Delta s^1 = a_{11}\Delta m_1 + a_{12}\Delta m_2 + \ldots + a_{1n}\Delta m_n$$

$$\Delta s^2 = a_{21}\Delta m_1 + a_{22}\Delta m_2 + \ldots + a_{2n}\Delta m_n$$

$$\ldots$$

$$\Delta s^N = a_{N1}\Delta m_1 + a_{N2}\Delta m_2 + \ldots + a_{Nn}\Delta m_n$$

or $$\begin{bmatrix} \Delta s^1 \\ \vdots \\ \Delta s^N \end{bmatrix} = \begin{bmatrix} a_{11} & \cdots & a_{1n} \\ & \ddots & \\ a_{N1} & \cdots & a_{Nn} \end{bmatrix} \begin{bmatrix} \Delta m_1 \\ \vdots \\ \Delta m_n \end{bmatrix}$$

When N=n, if n equations are linearly independent, the solution is $$\begin{bmatrix} \Delta m_1 \\ \vdots \\ \Delta m_n \end{bmatrix} = \begin{bmatrix} a_{11} & \cdots & a_{1n} \\ & \ddots & \\ a_{N1} & \cdots & a_{Nn} \end{bmatrix} \begin{bmatrix} \Delta s^1 \\ \vdots \\ \Delta s^N \end{bmatrix}$$

When N>n, and the rank of coefficient matrix=n, the solution is obtained by minimizing $$\left\| \begin{bmatrix} \Delta s^1 \\ \vdots \\ \Delta s^N \end{bmatrix} - \begin{bmatrix} a_{11} & \cdots & a_{1n} \\ & \ddots & \\ a_{N1} & \cdots & a_{Nn} \end{bmatrix} \begin{bmatrix} \Delta m_1 \\ \vdots \\ \Delta m_n \end{bmatrix} \right\|$$

In this manner, a raw intensity change can be estimated by a linear combination of changes in non-defect related characteristics (metrology changes). As such, information about the non-defect related characteristics may be extracted even if a correlation between the image data for the patterned wafer and a single non-defect related characteristic cannot be observed, provided that the scattering is sensitive to changes in the non-defect related characteristics. For example, for an optics mode that is sensitive to more than one non-defect related characteristic, a correlation between the image data generated using that optics mode and a single non-defect related characteristic is unlikely to be observed directly from the image data. However, by taking more than one non-defect related characteristic into consideration as described above, any changes in any of the non-defect related characteristic(s) of interest can be extracted from the image data for the wafer (e.g., using a linear relationship of changes in multiple non-defect related characteristics and output generated using two or more sets of parameters of the inspection system).

Therefore, this approach may provide a more precise relationship between raw intensity and metrology. For example, the embodiments described herein can help to understand an error source (e.g., when a correlation approach is not accurate enough). In one such example, one may attempt to establish a correlation between scattered light and surface roughness of a thin film formed on a wafer. However, the thickness of the thin film may also affect the scattered light and therefore introduce error into the correlation between surface roughness and one or more attributes of the scattered light. Therefore, by taking into account both surface roughness and thin film thickness (even if thin film thickness is not a non-defect related characteristic of interest and will not be reported by the method) using a linear combination of the metrology variables as described above, a more precise relationship between one or more attributes of the scattered light and non-defect related characteristics of the patterned wafer can be used to determine the relative changes in any one or more non-defect related characteristics thereby providing a more accurate determination of the changes in any of the one or more non-defect related characteristics.

Furthermore, the number of non-defect related characteristics, changes in which are taken into account by the linear combination, may vary depending on the sensitivity with which the user would like the non-defect related characteristic to be monitored. For example, increasing the number of non-defect related characteristics, changes in which are taken into account by the method, may generally increase the accuracy with which the differences between the value of the non-defect related characteristic and the known value can be determined. In this manner, if a user wants to know the change in the width of a line to about 2 nm, which is a substantially small difference, other metrology changes may have to be included in the linear combination to achieve that level of accuracy.

The mathematical approach described above can be modified to take into account metrology variables from other layers on the wafer. For example, a previous layer (a layer of the wafer formed under the uppermost layer on the wafer) may have some impact on the scattering response measured for the wafer by the inspection system. As such, additional metrology terms for the previous layer can be incorporated into the equations described above to account for those metrology terms. However, the linear coefficients for the metrology terms from the previous layer may also be assumed to be substantially smaller than those for the current layer because the previous layer may produce a substantially weaker scattering response. Therefore, in many instances, the metrology terms from the previous layer may be ignored (e.g., depending on the residual error ignoring such terms may cause compared to the desired accuracy with which the non-defect related characteristic is to be monitored).

The method for extracting changes in non-defect related characteristic(s) from the scattering response that is used in the embodiments described herein may, therefore, vary depending on the one or more parameters of the inspection system (e.g., optics mode) used to generate the output for the patterned wafer. For example, as set forth above, $$\Delta S = a_1 \Delta M_1 + a_2 \Delta M_2 + \ldots + a_n \Delta M_n$$

Therefore, any variation in the measured scattering response may be dependent on changes in multiple non-defect related characteristics. However, the non-defect related characteristic of interest is ideally extractable from the image data directly, meaning as described above that the scattering mainly depends on a single non-defect related characteristic. Mathematically, for $M_i$ of interest, if one or more parameters (e.g., an optics mode) of an inspection system can be identified that maximizes $$\frac{|a_i|}{\sum_{j \neq i} |a_j|}$$

the contributions to the scattering response measured by those one or more parameters from non-defect related characteristics other than $M_i$ may be ignored. In this manner, the output that is used in the embodiments described herein to monitor the non-defect related characteristic may be generated using only one set of parameters since output generated using other sets of parameters is not needed to determine the differences between the value and the known value. As such, in one embodiment, generating the output is performed using only one set of parameters of the inspection system. The one set of parameters may correspond to the one selected mode.

If the dependency to other non-defect related characteristics cannot be eliminated, output generated by multiple sets of parameters (e.g., scans/modes) may be needed since the response involves multiple non-defect related characteristics. In this manner, in another embodiment, generating the output is performed such that the output is generated using more than one set of parameters of the inspection system. Each of the more than one set of parameters may correspond to one mode. In addition, generating the output using more than one set of parameters may be performed in one or more scans (e.g., depending on the differences between the sets of parameters). For example, with some inspection systems, two passes may be performed with different bands/modes to gather the information that is used to separate two non-defect related characteristics if they interfere with each other in any particular band/mode of the inspection system. However, the optics modes can be selected as described above to reduce the number of non-defect related characteristics on which the scattering response is dependent. Therefore, the number of equations and the number of sets of parameters needed to determine the change in the non-defect related characteristic of interest may be reduced and even minimized, which will increase the throughput and speed of the methods. In addition, to minimize the throughput due to multiple scans, another approach is to only calculate sampled points for each die or each field. For example, the non-defect related characteristic can typically be considered unchanged within a die or reticle field, unless there are actual measurements of the non-defect related characteristic within the die or field, which is atypical. Therefore, there may be discrete areas within each die or field across the whole wafer at which the non-defect related characteristics are fitted to the observed attribute of the output at those locations. A surface metrology map for the wafer can then be interpolated from the calculated points. Furthermore, the computation cost should be relatively small if the calculations (e.g., inverse matrix/least square) are performed offline.

In this manner, the embodiments described herein provide a systematic way of extracting changes in non-defect related characteristic(s) from a raw image or image data generated for a patterned wafer by an inspection system. Furthermore, since the assumptions for the perturbation theory are not limited to any particular inspection system, the embodiments described herein may be implemented using inspection systems such as the 28xx and Puma systems as well as other tools such as macro inspection systems and electron beam inspection and/or review systems. Examples of such macro inspection systems and electron beam inspection and/or review systems include the LDS3xxx systems, eSxx systems, and eDR-xxxx systems, which are commercially available from KLA-Tencor.

In an additional embodiment, determining the differences includes simultaneously determining the differences between the value and the known value and differences between a value of at least one additional non-defect related characteristic of the patterned wafer and a known value of the at least one additional non-defect related characteristic of the different patterned wafer based on the differences between the one or more attributes of the output and the one or more attributes of the other output. In this manner, the method may include extracting multiple metrology signals. In particular, the method may include extracting multiple metrology signals from patterned wafer inspection systems. In other words, the method uses a wafer inspection tool to extract multitudes of metrology data of a patterned wafer. Simultaneously determining the differences between the values of two or more non-defect related characteristics and the known values of the two or more non-defect related characteristics may be performed as described herein (e.g., using a linear combination of changes in two or more non-defect related characteristics or multiple, different correlations, each between one or more attributes of the output and differences in the value of a non-defect related characteristic and a known value).

In one embodiment, the method includes generating the other output of the inspection system for the different patterned wafer by using the inspection system to scan the different patterned wafer. In this manner, the method may include calibration with a wafer with known metrology measurement(s). The other output may be generated as described herein. Generating the other output of the inspection system for the different patterned wafer may be performed using only the one or more parameters of the inspection system that are selected for use in the embodiments described herein. Alternatively, the other output may be generated using different sets of parameters of the inspection system such that the other output may be used to select the set or sets of parameters to be used to generate the output in the embodiments described herein. The metrology measurement(s) of the different patterned wafer may include any measurement(s) of any of the non-defect related characteristics described herein. In addition, the metrology measurement(s) may be performed on only those patterned features for which a non-defect related characteristic will be monitored (i.e., patterned features of interest) or patterned features that are selected as described herein. Alternatively, the metrology measurement(s) may be performed on all or some of the different types of patterned features formed on the different patterned wafer such that the patterned features that are most suitable for use in the embodiments described herein can be determined using the metrology measurement(s). Furthermore, the metrology measurement(s) may include any suitable metrology measurement(s) that can be performed using any suitable metrology process(es) using any suitable metrology system(s).

In another embodiment, the method includes generating the other output of the inspection system for the different patterned wafer by simulating the other output that would be generated by the inspection system for the different patterned wafer. In this manner, the method may include calibration through simulation. For example, the patterned features on the different patterned wafer may be fed into an EM simulator that combines the non-defect related characteristic to be sensed into the definition of the patterned features and simulates the inspection system response (i.e., the other output) for the set or sets of parameters of the inspection system that will be used to generate the output for the patterned wafer. For example, the patterned feature layer information along with expected variations in the non-defect related characteristic may be passed as input to an EM simulator (such as an RCWA or FDTD simulator that solves Maxwell's equations). The EM simulator may be run on the selected die cell(s) in the layout of the die or the field to find the far-field amplitude and phase resulting from the metrology modified patterned features. The results of running the EM simulator and the information about the inspection system may be used to process the EM files for the inspection system. For example, the amplitude and phase files may be combined with the desired inspection system to output the possible signals as a function of the parameters (e.g., band/mode) of the inspection system to be used for generating the output for the patterned wafer thereby generating other output for the different patterned wafer.

Each of the embodiments of the method described above may include any other step(s) of any method(s) described herein. In addition, each of the embodiments of the method described above may be performed by any system embodiments described herein.

Any of the methods described herein may include storing results of one or more steps of one or more methods described herein in a storage medium. The results may include any of the results described herein. The results may be stored in any manner known in the art. In addition, the storage medium may include any storage medium described herein or any other suitable storage medium known in the art. After the results have been stored, the results can be accessed in the storage medium and used by any of the method or system embodiments described herein or any other method or system. Furthermore, the results may be stored "permanently," "semi-permanently," temporarily, or for some period of time. For example, the storage medium may be random access memory (RAM), and the results may not necessarily persist indefinitely in the storage medium. In addition, the results of any of the step(s) of any of the method(s) described herein can be stored using systems and methods such as those described in commonly owned U.S. patent application Ser. No. 12/234,201 by Bhaskar et al. filed Sep. 19, 2008, which is incorporated by reference as if fully set forth herein.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Another embodiment relates to a computer-readable medium that includes program instructions executable on a computer system for performing a computer-implemented method for monitoring a non-defect related characteristic of a patterned wafer. One such embodiment is illustrated in FIG. 1. In particular, as shown in FIG. 1, computer-readable medium 10 includes program instructions 12 executable on computer system 14. The computer-implemented method includes generating output responsive to light from a patterned wafer using an inspection system. Generating the output may be performed according to any of the embodiments described herein. The output may include any of the output described herein. The inspection system may be configured as described herein.

The computer-implemented method also includes determining differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic. Determining the differences may be performed according to any of the embodiments described herein. The value of the non-defect related characteristic may include any such values described herein. The known value of the non-defect related characteristic may include any such values described herein. The non-defect related characteristic may include any of the non-defect related characteristics described herein. The one or more attributes of the output and the other output may include any such attribute(s) described herein. The other output may include any of the other output described herein. The different patterned wafer may include any of the different patterned wafers described herein. The computer-implemented method may include any other step(s) of any other embodiment(s) described herein.

Program instructions 12 implementing methods such as those described herein may be stored on computer-readable medium 10. The computer-readable medium may be a storage medium such as a read-only memory, a random access memory, a magnetic or optical disk, or a magnetic tape. In addition, the computer-readable medium may include any other suitable computer-readable medium known in the art.

Computer system 14 may take various forms, including a personal computer system, mainframe computer system, workstation, image computer, parallel processor, or any other device known in the art. In general, the term "computer system" may be broadly defined to encompass any device having one or more processors, which executes instructions from a memory medium. The computer system may also be included in an inspection system. The inspection system may be configured as described herein.

Figure 2:
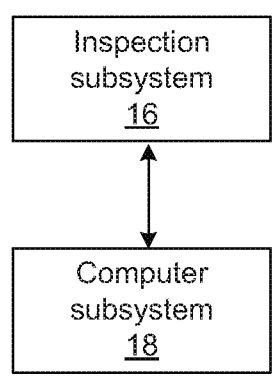
FIG. 2 is a block diagram illustrating one embodiment of a system configured to monitor a non-defect related characteristic of a patterned wafer.

An additional embodiment relates to a system configured to monitor a non-defect related characteristic of a patterned wafer. One embodiment of such a system is shown in FIG. 2. As shown in FIG. 2, the system includes inspection subsystem 16. The inspection subsystem is configured to generate output responsive to light from a patterned wafer. The inspection subsystem may be configured to generate the output according to any of the embodiments described herein. The output may include any of the output described herein.

Inspection subsystem 16 may include any suitable inspection subsystem such as those included in commercially available inspection systems. Examples of commercially available inspection systems that include suitable inspection subsystems include the 28xx systems and the Puma 90xx and 91xx series tools, which are commercially available from KLA-Tencor. In addition, the inspection subsystem may be an inspection subsystem configured for DF inspection of a patterned wafer and/or BF inspection of a patterned wafer. Furthermore, an existing patterned wafer inspection system may be modified (e.g., a computer subsystem of the inspection system may be modified) such that the existing inspection system, including its inspection subsystem, can be used as a system described herein. The inspection subsystem may be configured to perform any other step(s) of any method(s) described herein.

The system also includes computer subsystem 18. The computer subsystem is configured to determine differences between a value of a non-defect related characteristic of the patterned wafer and a known value of the non-defect related characteristic based on differences between one or more attributes of the output and one or more attributes of other output of the inspection system for a different patterned wafer having the known value of the non-defect related characteristic. The computer subsystem may be configured to determine the differences according to any of the embodiments described herein. The value of the non-defect related characteristic may include any such values described herein.

The known value of the non-defect related characteristic may include any such values described herein. The non-defect related characteristic may include any of the non-defect related characteristics described herein. The one or more attributes of the output and the other output may include any such attribute(s) described herein. The other output may include any of the other output described herein. The different patterned wafer may include any of the different patterned wafers described herein. The computer subsystem may be further configured as described above with respect to computer system 14 shown in FIG. 1. In addition, the computer subsystem may be configured to perform any other step(s) of any method(s) described herein. The embodiment of the system described above may be further configured as described herein.

Further modifications and alternative embodiments of various aspects of the invention may be apparent to those skilled in the art in view of this description. For example, methods and systems for monitoring a non-defect related characteristic of a patterned wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for monitoring a non-defect related characteristic of a patterned wafer, comprising:
   generating output responsive to light scattered from a patterned wafer using an inspection system;
   determining a change between the output and other output of the inspection system for a different patterned wafer having known values of first and second non-defect related characteristics, wherein the patterned wafer has unknown values of the first and second characteristics, and wherein the output used to determine the change is generated in an area on the patterned wafer in which local variations in the first and second characteristics are negligible thereby rendering the change between the output and the other output equal to a linear combination of a change between the unknown and known values of the first characteristic and a change between the unknown and known values of the second characteristic; and
   determining the change between the unknown and known values of the first characteristic based on the change between the output and the other output.

2. A system configured to monitor a non-defect related characteristic of a patterned wafer, comprising:
   an inspection subsystem configured to generate output responsive to light scattered from a patterned wafer; and
   a computer subsystem configured for:
      determining a change between the output and other output of the inspection subsystem for a different patterned wafer having known values of first and second non-defect related characteristics, wherein the patterned wafer has unknown values of the first and second characteristics, and wherein the output used to determine the change is generated in an area on the patterned wafer in which local variations in the first and second characteristics are negligible thereby rendering the change between the output and the other output equal to a linear combination of a change between the unknown and known values of the first characteristic and a change between the unknown and known values of the second characteristic; and
      determining the change between the unknown and known values of the first characteristic based on the change between the output and the other output.

3. The system of claim 2, wherein the area on the patterned wafer is less than about 100 microns.

4. The system of claim 2, wherein the area on the patterned wafer comprises a single type of patterned features.

5. The system of claim 2, wherein the area on the patterned wafer comprises only one of multiple reticle fields on the patterned wafer.

6. The system of claim 5, wherein the multiple reticle fields are printed on the wafer at different combinations of focus and exposure values.

7. The system of claim 2, wherein the change between the output and the other output comprises a change in raw intensity values of the output and the other output.

8. The system of claim 2, wherein the change between the output and the other output comprises a change in mean intensity values of the output and the other output.

9. The system of claim 2, wherein the inspection subsystem is further configured to generate the output with multiple parameters of the inspection subsystem, and wherein the computer subsystem is further configured for measuring changes in the first characteristic across the different patterned wafer, determining a correlation between additional output generated for the different patterned wafer across the multiple parameters of the inspection system and the changes in the first characteristic, and selecting one or more of the multiple parameters used for generating the output and the other output based on the determined correlation.

10. The system of claim 2, wherein the inspection subsystem does not apply Fourier filtering to the output to thereby maintain portions of the output responsive to the light scattered from patterned features on the patterned wafer.

11. The system of claim 2, wherein the computer subsystem is further configured for:
   determining a change between the output generated in a first area on the patterned wafer and additional output of the inspection subsystem generated in a second area on the patterned wafer, wherein the patterned wafer has unknown values of the first and second characteristics in the first and second areas, wherein the first and second areas are formed on the wafer with different exposure conditions, and wherein the local variations in the first and second characteristics are negligible in the first and second areas thereby rendering the change between the output and the additional output equal to a linear combination of a change between the unknown values of the first characteristic in the first and second areas and a change between the unknown values of the second characteristic in the first and second areas; and
   determining the change between the unknown values of the first characteristic in the first and second areas based on the changes between the output and the additional output.

12. The system of claim 2, wherein patterned features formed on the patterned wafer are not resolved in the output generated for the patterned wafer by the inspection subsystem.

13. The system of claim 2, wherein the inspection subsystem is further configured to generate the output and the other output using different modes of the inspection subsystem, and wherein the output used to determine the change is generated in the area on the patterned wafer thereby rendering changes between the output and the other output generated using the different modes equal to different linear combinations, respectively, of the change between the unknown and known values of the first characteristic and the change between the unknown and known values of the second characteristic.

14. The system of claim 13, wherein determining the change between the unknown and known values of the first characteristic is based on the changes between the output and the other output generated using the different modes.

15. The system of claim 2, wherein the computer subsystem is further configured for determining the change between the unknown and known values of the second characteristic based on the change between the output and the other output.

16. The system of claim 2, wherein the different patterned wafer is a physical version of the different patterned wafer.

17. The system of claim 2, wherein the different patterned wafer is a simulated version of the different patterned wafer.

18. The system of claim 2, wherein the inspection subsystem is further configured to generate the output using only one set of parameters of the inspection subsystem.

19. The system of claim 2, wherein the computer subsystem is further configured as a virtual inspector.

20. A non-transitory computer-readable medium, comprising program instructions executable on a computer system for performing a computer-implemented method for monitoring a non-defect related characteristic of a patterned wafer, wherein the computer-implemented method comprises:

generating output responsive to light scattered from a patterned wafer using an inspection system;

determining a change between the output and other output of the inspection system for a different patterned wafer having known values of first and second non-defect related characteristics, wherein the patterned wafer has unknown values of the first and second characteristics, and wherein the output used to determine the change is generated in an area on the patterned wafer in which local variations in the first and second characteristics are negligible thereby rendering the change between the output and the other output equal to a linear combination of a change between the unknown and known values of the first characteristic and a change between the unknown and known values of the second characteristic; and determining the change between the unknown and known values of the first characteristic based on the change between the output and the other output.

* * * * *